(12) United States Patent
Berndtsson

(10) Patent No.: US 8,012,432 B2
(45) Date of Patent: *Sep. 6, 2011

(54) DISPOSABLE APPARATUS FOR USE IN BLOOD TESTING

(75) Inventor: Ingemar Berndtsson, Sollentuna (SE)

(73) Assignee: Boule Medical AB, Stockholm (SE)

( * ) Notice: Subject to any disclaimer, the term of this patent is extended or adjusted under 35 U.S.C. 154(b) by 1385 days.

This patent is subject to a terminal disclaimer.

(21) Appl. No.: 11/493,697

(22) Filed: Jul. 27, 2006

(65) Prior Publication Data

US 2006/0263246 A1    Nov. 23, 2006

Related U.S. Application Data

(63) Continuation of application No. 10/849,239, filed on May 20, 2004, now Pat. No. 7,335,339.

(51) Int. Cl.
*B01L 3/00* (2006.01)

(52) U.S. Cl. ......... 422/547; 422/501; 422/504; 422/565

(58) Field of Classification Search ............... 422/68.1, 422/73, 99, 100, 102, 501, 502, 504, 537, 422/547, 560, 561, 565; 436/62, 63, 66, 436/69, 70, 174–180

See application file for complete search history.

(56) References Cited

U.S. PATENT DOCUMENTS

| | | | |
|---|---|---|---|
| 4,799,393 A | 1/1989 | Uffenheimer | |
| 5,077,017 A | 12/1991 | Gorin et al. | |
| 5,104,813 A | 4/1992 | Besemer et al. | |
| 5,230,866 A * | 7/1993 | Shartle et al. | 422/103 |
| 5,316,730 A | 5/1994 | Blake et al. | |
| 5,558,838 A | 9/1996 | Uffenheimer | |
| 5,652,149 A | 7/1997 | Mileaf et al. | |
| 6,016,712 A | 1/2000 | Warden et al. | |
| 6,232,127 B1 * | 5/2001 | Lane et al. | 436/69 |
| 6,284,548 B1 | 9/2001 | Berndtsson | |
| 6,387,328 B1 | 5/2002 | Berndtsson | |
| 7,335,339 B2 * | 2/2008 | Berndtsson | 422/102 |

FOREIGN PATENT DOCUMENTS

| | | |
|---|---|---|
| WO | WO-95/18962 A1 | 7/1995 |
| WO | WO-98/22797 A1 | 5/1998 |
| WO | WO-99/01742 A1 | 1/1999 |
| WO | WO-01/75416 A1 | 10/2001 |

* cited by examiner

*Primary Examiner* — Jill Warden
*Assistant Examiner* — Dwayne K Handy
(74) *Attorney, Agent, or Firm* — Birch, Stewart, Kolasch & Birch, LLP

(57) ABSTRACT

A disposable apparatus for use in blood testing and being adapted for simultaneous dilution of a blood sample into two different dilution ratios, said apparatus including a block-shaped housing having integrated therein a first and a second receptacle, one of which as a first blood sample receiver being adapted to receive a blood sample; a first and a second container, each containing a defined volume of a diluting agent; a valve including a valve body having three valve body channels extending therethrough and being positionable in three distinct positions, one of which putting the receptacles in simultaneous communication with a respective one of the containers through pairs of the channels; and displacers for displacing the diluting agent and the diluted sample through said channels between said containers and said receptacles.

26 Claims, 12 Drawing Sheets

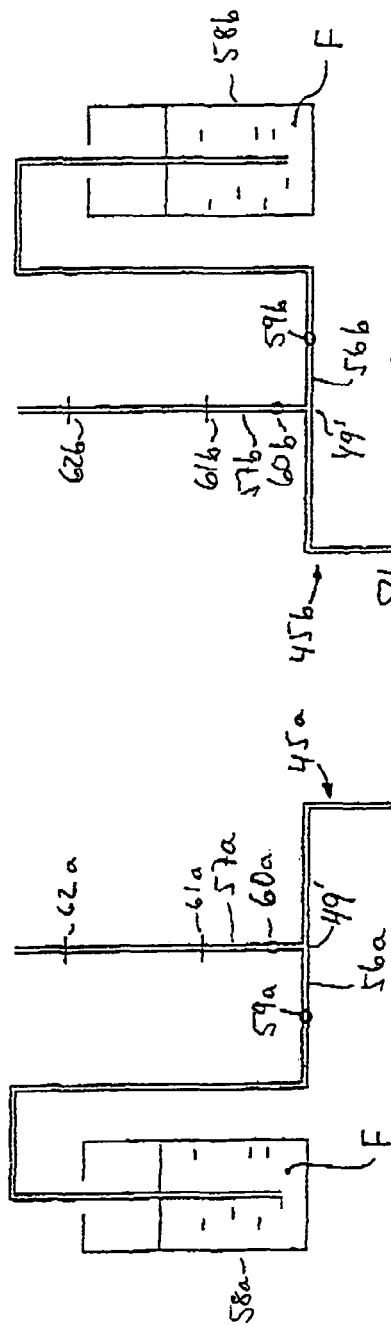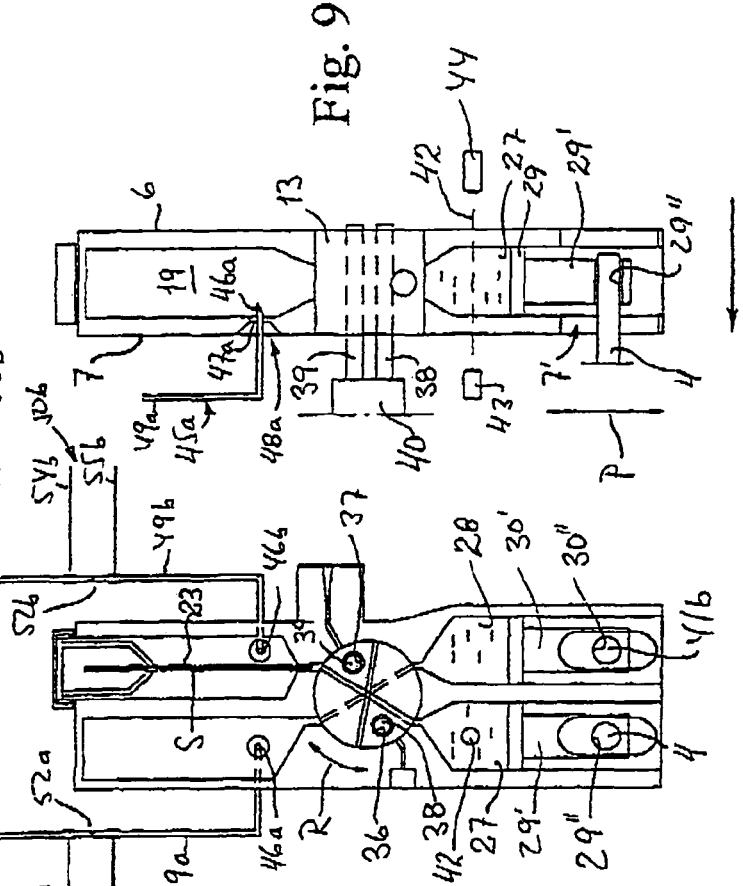
Fig. 8
Fig. 9

DISPOSABLE APPARATUS FOR USE IN BLOOD TESTING

CROSS-REFERENCE TO RELATED APPLICATION

The present application is a Continuation of Application Ser. No. 10/849,239, filed May 20, 2004, now U.S. Pat. No. 7,335,339 and claims priority under 35 U.S.C. §119 to Swedish Patent Application No. 2001-0103877-7, filed Nov. 21, 2001, the entire contents of which are hereby incorporated by reference.

BACKGROUND OF THE INVENTION

1. Field of the Invention

The present invention concerns a disposable apparatus for use in blood testing.

2. Description of Background Art

When making blood tests in the field, it is a desire to perform such tests with simple but reliable apparatus that can be handled even by relatively untrained personnel. Still, there exists the requirement that a blood sample shall be taken and handled under strict hygienic conditions, and that neither the sample itself or residues thereof, nor diluting or flushing liquids used when testing the sample shall risk to be contacted by humans. Thus, there shall be no waste matter and all contaminated material shall remain within the apparatus.

It is known in the state of art to count blood cells by causing a volume of diluted blood sample to pass a so-called capillary, i.e., an extremely small hole, generally in a ruby, the hole having a diameter considerably larger than the size of a blood cell, typically 80 µm. A voltage is applied over the capillary, and, when a blood cell passes through the hole, the electrical resistance changes. This is because the cells can be regarded as insulators. Each change in resistance can be detected by suitable electronic equipment, and the sum of all changes detected corresponds to the number of blood cells having passed through the capillary. In order to obtain the concentration of cells in the original sample, the concentration of cells in the diluted sample is multiplied by the dilution factor, typically 1:40000 when counting of red blood cells (RBC) is concerned. It is obvious, that measuring of sample volumes and dilution liquid volumes must be performed in an accurate and repeatable way such that not only a correct degree of dilution can always be guaranteed but also a thorough and uniform mixing of the two volumes is ensured.

A disposable sampling device for an apparatus for counting particles contained in a liquid, such as blood cells in a blood sample, is known from WO 99/01742. This device is capable of making one diluting step.

A blood testing apparatus for performing dilution of a small defined volume of blood sample contained in a capillary tube is described in U.S. Pat. No. 6,284,548. The dilution involves a pre-dilution step and a final dilution step.

A device for diluting and mixing a liquid sample, such as a blood sample for performing a CRP test, is described in WO 01/75416. The sample is contained in a capillary tube and is mixed in a first step with a diluting agent to provide a diluted sample. In a second step, a third medium, such as antibodies, may be mixed with the diluted sample.

Even if some of the prior art devices are capable of making two dilutions, none of them is capable of making two simultaneous dilutions to different dilution ratios, which is desirable in order to perform, e.g., simultaneous counting of white and red blood cells.

SUMMARY AND OBJECTS OF THE INVENTION

It is a main object of the present invention, thus, to provide a disposable apparatus for use in blood testing, which allows simultaneous dilution of a blood sample to two defined dilutions ratios. Also, in order to avoid waste, the disposable apparatus shall be capable of retaining all contaminated material within itself. It is also an object of the present invention to propose an instrument for use with the apparatus.

To fulfill the main object above, the present invention proposes a disposable apparatus for use in blood testing and being adapted for simultaneous dilution of a blood sample into two different dilution ratios, said apparatus including a block-shaped housing having integrated therein: a first and a second receptacle, one of which, as a first blood sample receiver, being adapted to receive a blood sample; a first and a second container, each containing a defined volume of a diluting agent; a valve including a valve body having three valve body channels extending therethrough and being positionable in three distinct positions, one of which bringing the receptacles in simultaneous communication with a respective one of the containers through pairs of the channels; and displacers for displacing the diluting agent and the diluted sample through said channels between said containers and said receptacles. The displacers may be pistons movable in cylinders provided in the housing, or, an external source of pressure may be utilized to displace the diluting agent and the diluted sample.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described in connection with an embodiment thereof utilizing a turning valve, and pistons as displacers, reference being made to the accompanying schematic drawings, wherein:

FIG. 8 is a front view of the apparatus as shown in FIGS. 5 and 7 connected to schematically shown external fluid conduits and valve and plunge actuating means of a test instrument;

FIG. 9 is a side view of the apparatus as shown in FIG. 8 and parts of the test instrument;

DETAILED DESCRIPTION OF THE PREFERRED EMBODIMENTS

Figure 1:
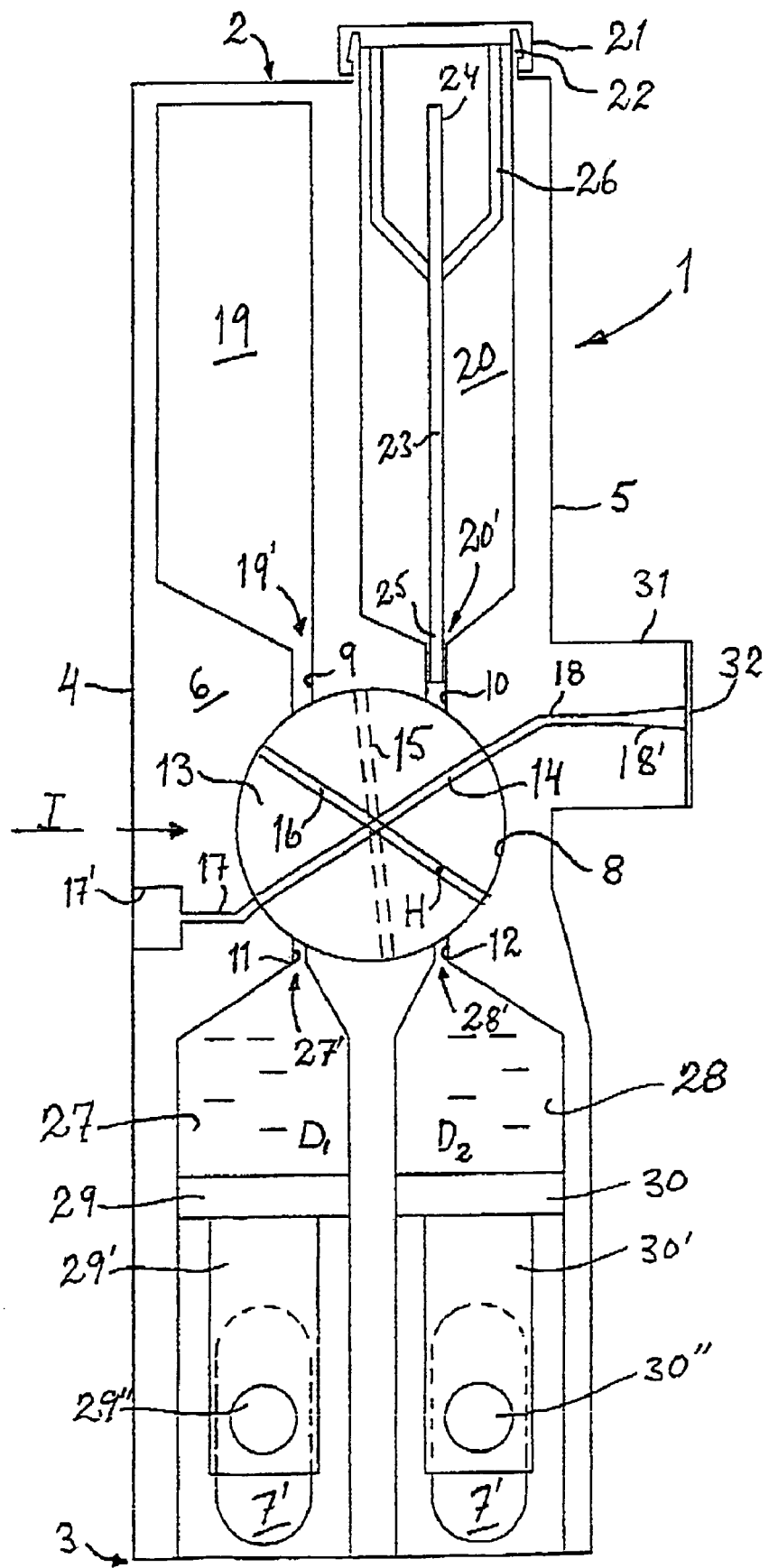
FIG. 1 is a front view showing the apparatus in its preparatory state including a capillary tube held by a cover.

It is evident for the skilled person that the present invention may as well be practiced utilizing a sliding valve instead of the turning valve specifically described. I the following description, the terms upper, lower, right, left etc., refer to the position of the apparatus shown in the various Figures.

The overall structure of the apparatus will first be described with reference to FIG. 1. It consists of a block-like housing 1 (see also the side view of FIG. 9) preferably made of a translucent, moldable material. The housing has an upper end 2, a bottom end 3, a left side wall 4, a right side wall 5, a front wall 6 and a rear wall 7 seen in FIG. 9 only.

In a central portion of the housing is provided a cylindrical hole 8. Two channels 9 and 10 extending towards the upper end 2 open in the hole 8 at spaced locations along its upper circumference. Correspondingly, two channels 11 and 12 extending towards the bottom end 3 open in the hole 8 at spaced locations along its lower circumference.

A turning valve body 13 dimensioned to fit into the hole 8 is placed therein so as to be rotatable between at least three distinct positions. Three separate channels, a first channel 14, a second channel 15 and a third channel 16, extend through the valve body between mutually diametrically opposed positions along the circumference of the valve body. The channels are angularly spaced such that there is a substantially 60° angular distance between them along the circumference. By turning the valve body, the channels 14-16 may be positioned so as to cross-wise put the channels 9/12 and 10/11 in communication with one another.

The valve body is shown in FIG. 1 in a first rotational position I. In this position, the preparatory position, none of the channels 14-16 communicate with the channels 9/12 and 10/11. It can be seen however, that one end of the channel 14 communicates with a channel 17 extending between a position along the left portion of the circumference of the hole 8 and the left side wall 4, and that its opposite end communicates with a channel 18 extending between an opposed portion along the right portion of the circumference of the hole 8. The purpose of this communication will be explained later with reference to FIGS. 6 and 7.

In the upper portion of the housing 1 are formed two receptacles 19, 20, preferably formed like parallel bores. A first one of these, receptacle 19, has its lower end 19' connected to the channel 9. Its upper end is shown to be closed, but it may as well be open and closed by any suitable removable cover. A second one of the receptacles, receptacle 20, has its lower end 20' connected to the channel 10. Its upper end is closed by a preferably circular cover 21 snapped into engagement with a hook-like protrusion 22 formed at the upper end 2 of the housing.

The cover 21 is shown to carry a capillary tube 23 having an upper end 24 and a lower end 25. The tube is mounted in the cover by means of ribs 26 depending from the cover such that the upper end of the tube opens in an open space between the ribs communication with atmosphere.

As an alternative option, there may be provided a separate cover 21 to close the receptacle 20 and a separate combination of a cover 21 and a capillary tube as shown.

In the lower portion of the housing 1 are formed two parallel cylinders 27, 28. A first one of these, cylinder 27, has its upper end 27' connected to the channel 11. A second of the cylinders 28 has its upper end 28' connected to the channel 12. A first piston 29 is slidably reciprocatingly movable along the cylinder 27. A second piston 30 is slidably reciprocatingly movable along the cylinder 28. The pistons have piston rods 29', 30', respectively, each having in a lower end thereof a through hole 29", 30", respectively. The holes 29", 30" are accessible through vertically extending apertures 7' in the rear wall 7 of the housing.

The right hand wall 5 of the housing is provided with a cylindrical protrusion 31, in the centre of which opens the channel 18 with a slightly widening mouth portion 18'. An elastic diaphragm 32 seals the mouth portion 18'. In the preparatory state of the apparatus, the cylinders 27 and 28 are both filled with well-defined volumes, typically 2 ml, of diluting agent $D_1$, $D_2$, respectively, typically isotonic sodium chloride solution. Furthermore, the channel 16 is filled with an appropriate amount of a haemolysis agent H, which may be in a dried or a fluid state. In the first position I of the valve body 13, where the ends of the channel 16 are located at a distance from any one of the housing channels 9, 12, 17, 18, the haemolysis agent H is effectively prevented from escaping the channel 16.

Figure 2:
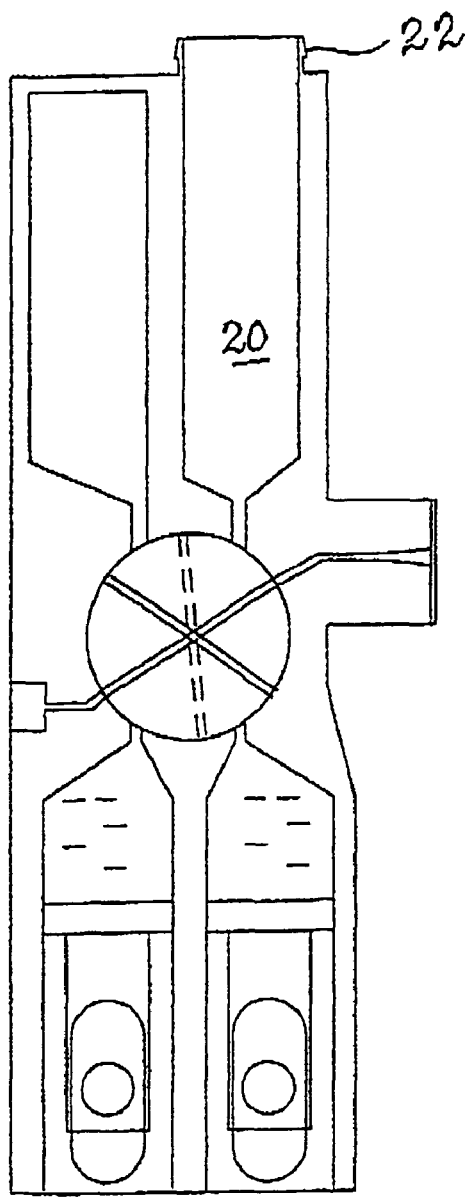
FIG. 2 is a corresponding view showing the apparatus with its capillary tube and cover removed.
Figure 3:
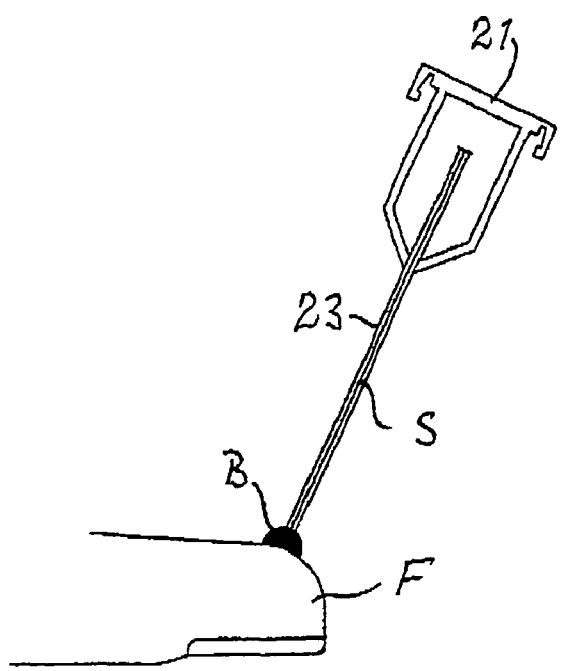
FIG. 3 is a view showing the removed capillary tube in a position receiving a blood sample from punctured finger tip.
Figure 4:
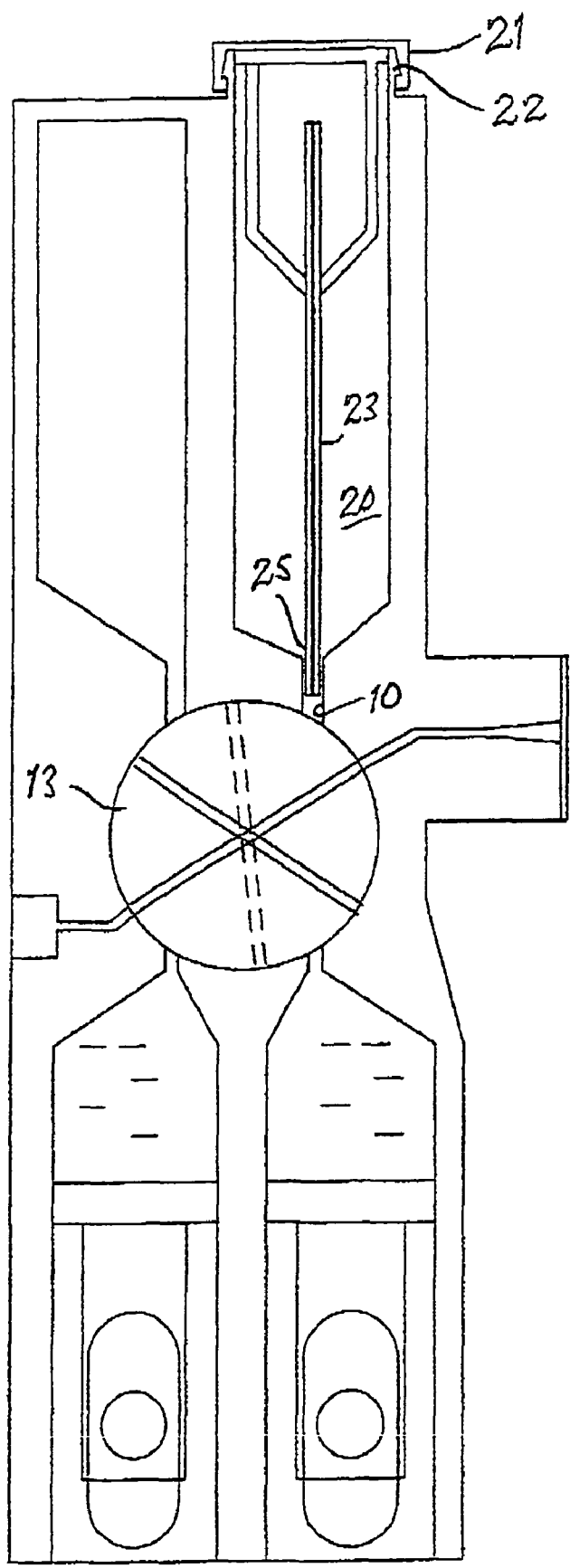
FIG. 4 is a view corresponding that of FIG. 2 showing the apparatus with the capillary tube and its blood sample relocated in its original position within the apparatus.

In a first mode of operation shown in FIGS. 2 and 3, the apparatus is used in finger tip blood sampling. The cover 21—and with it the capillary tube 23—is removed from the housing 1, and a blood sample S is taken with the capillary tube as illustrated in FIG. 3. The tube is approached to a drop of blood B formed on a punctured finger tip F, and the drop is sucked up by capillary action to completely fill the tube with a defined volume of sample S. During this operation, the cover 21 serves as a handle, thus avoiding any contact with the sample. After the sample is taken, the capillary tube is re-inserted into the receptacle 20 as seen in FIG. 4, and the cover 21 is pushed down to snap into sealing contact with the protrusions 22. In this position, the lower end 25 of the capillary tube may be more (as shown) or less introduced into channel 10.

Figure 5:
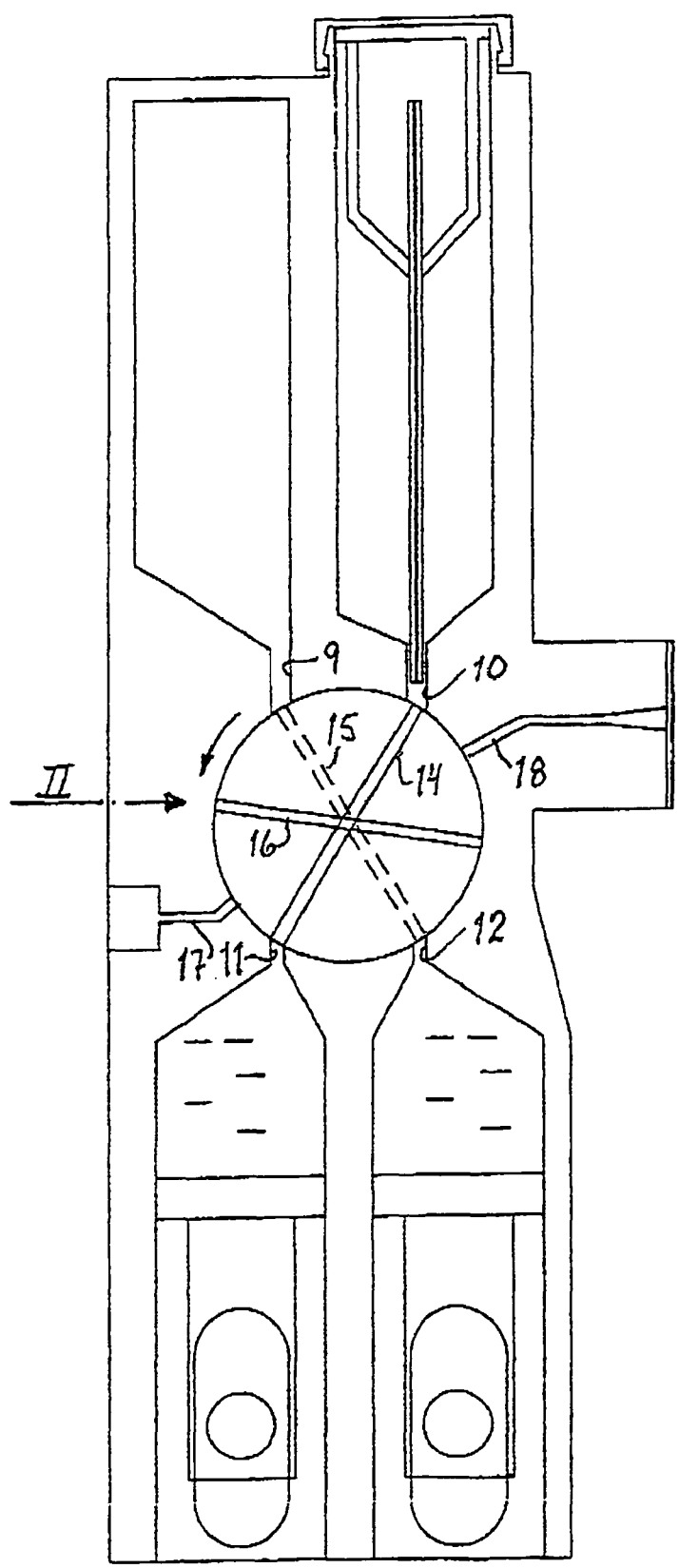
FIG. 5 is a front view of the apparatus as shown in FIG. 4 having the turning valve rotated one step to a second position.

In the state according to FIG. 4, the turning valve 13 is rotated one step counterclockwise to the second rotational position II shown in FIG. 5, where the housing channels 9 and 12 communicate through valve channel 15 and the housing channels 10 and 11 communicate through valve channel 14. In practice, the housing is placed in an associated instrument, as will be described later, for automatic performance of the valve rotation.

Figure 6B:
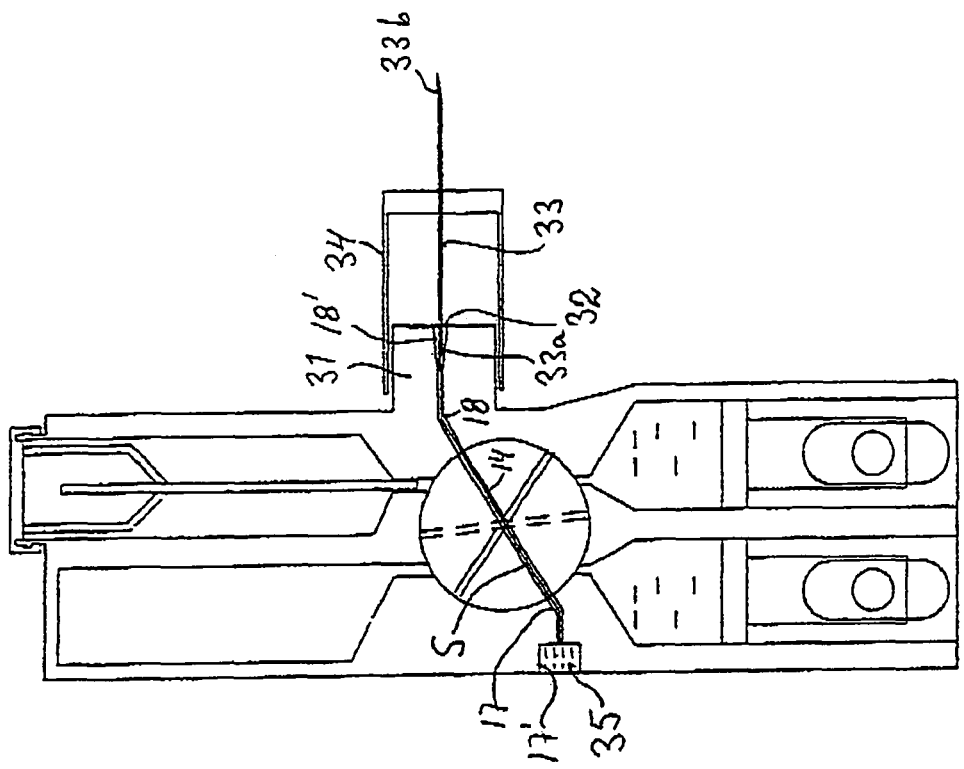
FIGS. 6a and b are front views showing the apparatus in its preparatory state according to FIG. 1 and illustrating a further possibility to charge the apparatus with a blood sample.
Figure 6A:
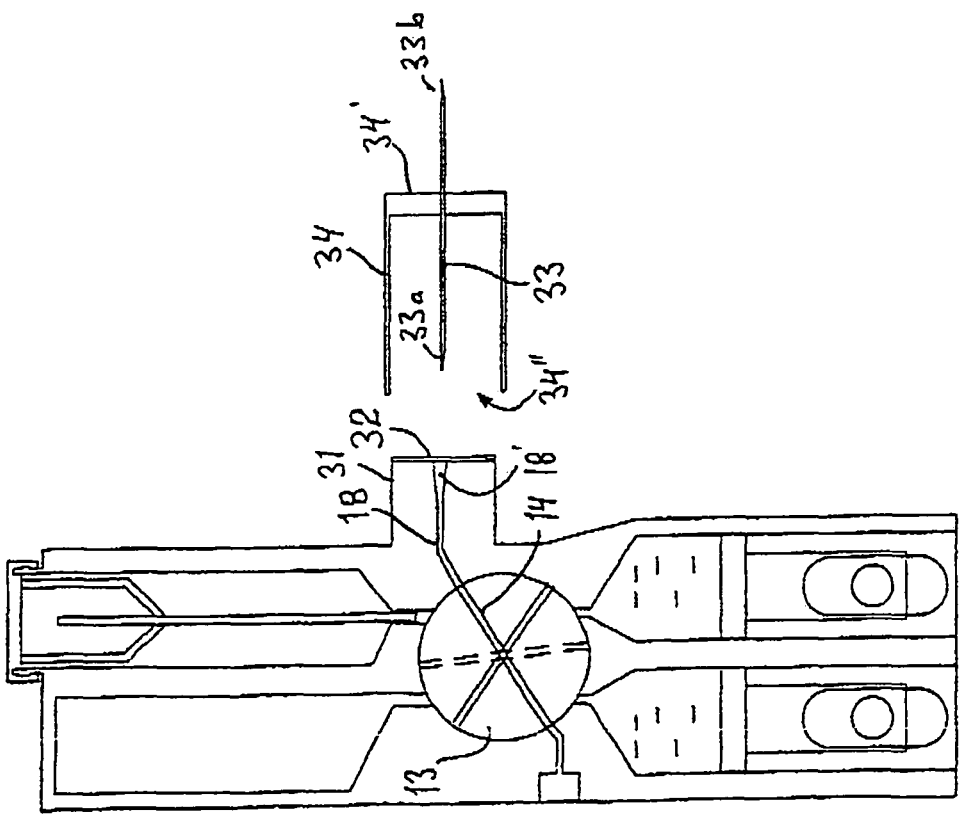

In a second mode of operation shown in FIGS. 6a and 6b, the apparatus is used in venipuncture sampling. When taking a venipuncture sample, blood is introduced into the channel 18 to pass into and through the valve body channel 14. This is suitable made by an injection needle or cannula 33 by which the diaphragm is pierced. Preferably, a so-called vacuutainer sleeve 34 is used, i.e., a device commonly used in connection with a so-called vacuutainer. A vacuutainer sleeve is a cylindrical hollow body having a bottom 34' centrally carrying the needle 33, and having an open end 34". The needle has both its end chamfered so as to provide sharpened points 33a, 33b. The exterior dimension of the protrusion 31 is adapted to the interior dimension of the open end 34" of the vacuutainer sleeve, so that the latter may be pushed onto the protrusion 31 with the needle point 33a penetrating the diaphragm 32 and being introduced into the channel mouth 18'. In this position, the housing 1 with the vacuutainer sleeve may be manipulated so as to bring the needle point 33b to puncture a vein. The venous pressure will force blood through the needle 33, the channel 18, the channel 14 into the channel 17 as seen in FIG. 6b, where a sample S is shown to occupy the interiors of the needle 33 and the channels 18, 14 and 17. A widened portion 17' of the channel 17 is suitably provided with a plug 35 of a material, such as a textile material, having the properties to allow air, but preventing blood flow therethrough. After the sample is taken, the needle point 33b is withdrawn from the punctured vein and, subsequently, the needle point 33a is withdrawn from the channel mouth 18' and from the pierced diaphragm 32. Due to the elasticity of the latter, it will seal itself and prevent any escape of blood from the portion of the sample within the channel 18.

Figure 7:
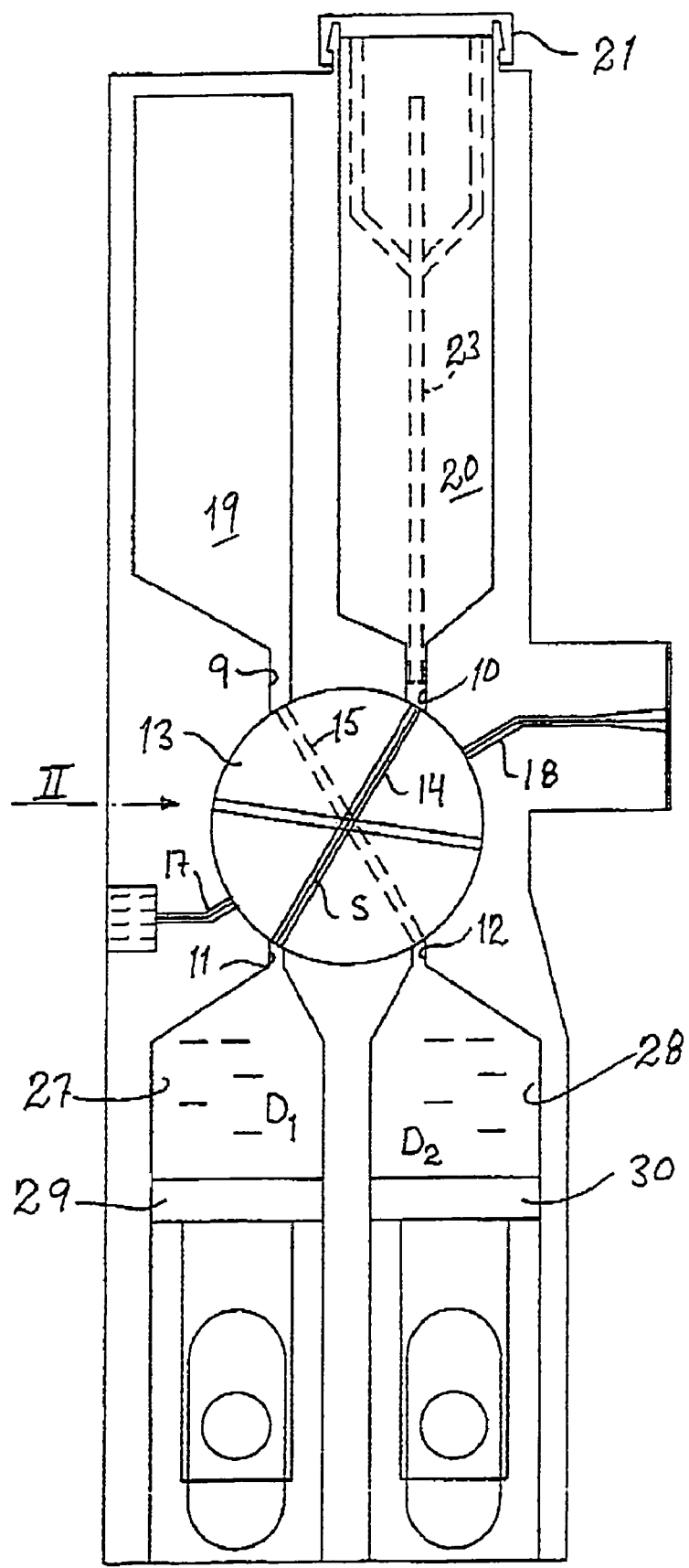
FIG. 7 is a view corresponding to that of FIG. 6b showing the apparatus with the turning valve rotated one step to a second position.

In the state according to FIG. 6b, the turning valve 13 is rotated one step counterclockwise to the second rotational position II shown in FIG. 7, thereby separating the defined volume of blood sample S contained within the channel 14 from the volumes contained within the housing channels 17 and 18, and further placing the housing channels 9 and 12 in mutual communication through the valve body channel 15 and the housing channels 10 and 11 in mutual communication through the valve body channel 14. In practice, the housing is placed in an associated instrument, as will be described later, for automatic performance of the valve rotation.

It is noted in FIG. 7, that the capillary tube 23 is shown in dotted lines to indicate its option in this mode, whereas the cover 21 is shown in full lines. It is furthermore noted, that the rotational positions II of the valve body 13 shown in FIGS. 5 and 7 are the very same, and that the only difference is that the blood sample S is within the capillary tube 23 in FIG. 5 and within the valve body channel 14 in FIG. 7. In this position, common to both modes of operation, both pistons 29 and 30 are operated in a positive (i.e., upward) direction so as to displace the defined volume of diluting agent $D_1$ from the cylinder 27 through the channels 11, 14 and 10 into the receptacle 20, and so as to displace the defined volume of diluting agent $D_2$ from the cylinder 28 through the channels 12, 15 and 9 into the receptacle 19.

Turning now to FIGS. 8 and 9, these figures show the apparatus housing 1 placed in an instrument having means for rotating the turning valve body 13 and for operating the pistons 29, 30, as well as means for performing certain measurements.

As shown in FIG. 8, the valve body 13 is provided with two diametrically opposed holes 36, 37. When the apparatus housing is placed in the instrument, two operating arms 38, 39 of a rotatable valve operating member 40 engage in a respective one of these holes as seen in the side view of FIG. 9. Simultaneously, two piston operating arms 41a, 41b engage in a respective one of the through holes 29", 30" in the piston rods 29', 30'. The valve operating member 40 is rotatable in the directions of the double arrow R in FIG. 8, and the piston operating arms 40, 41 are vertically movable so as to move the pistons in the directions of the double arrow P in FIG. 9. Such movement is preferably simultaneous for both pistons.

FIG. 8 shows a situation corresponding to that of FIG. 5, i.e., with the blood sample S within the capillary tube 23. An upward stroke of the piston 29 will direct the diluting agent $D_1$ through the channel 10 (see FIG. 10) and at least partly through the capillary tube 23 having its lower end 25 introduced therein. Consequently, the sample S will be displaced upwardly from the capillary tube and flow from its upper end 24 down into the receptacle 20, where it will mix with parts of the diluting agent having passed through the annular space 10' formed between the lower end 25 of the capillary tube and the channel 10. A subsequent downward stroke of the piston 29 will withdraw the mixture $(S+D_1)$ of sample S and diluting agent $D_1$ from the receptacle 20 through the annular space 10' to flow into the cylinder 27. Further subsequent strokes according to the arrow P will complete this mixing operation, which is a first stage mixing operation. Simultaneous strokes of the piston 30 in the directions P will only force the diluting agent $D_2$ from the cylinder 28 into the receptacle 19 and back.

In the second mode of operation, an upward stroke of piston 29 will displace the diluting agent $D_1$ through the channel 14 and consequently bring along the defined volume of sample S contained within the channel 14 directly into the recipient 20 in case there is no capillary tube 23 present, and partly through such tube if one is present. Subsequent strokes according to arrow P will complete the first stage mixing operation as in the first mode of operation.

In FIG. 8 is shown a circle indicating a light path 42 through the cylinder 27. This light path is also shown in FIG. 9 to extend between a light source 43 and a detector 44. The light path may be used to measure firstly a reference value of the diluting agent $D_1$ and subsequently a value after the first stage diluting step, i.e., of the diluted sample $(S+D_1)$.

Figure 10:
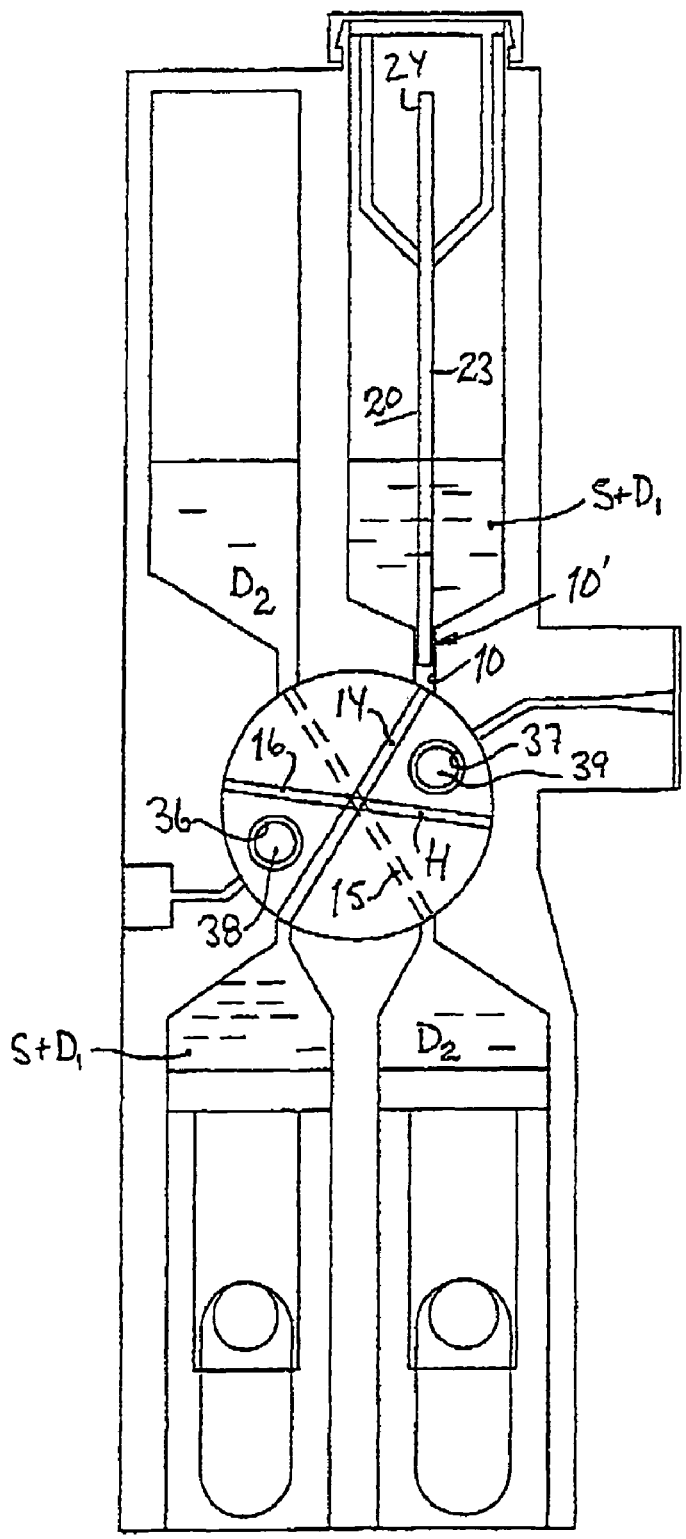
FIG. 10 is a front view of the apparatus shown in the valve position of FIGS. 5, 7 and 8 and with its plungers displaced to their extreme positive position.

FIG. 10 shows the situation during the first mixing operation when the pistons are reciprocating in the directions of arrows P to complete the mixing. The pistons are halted in an intermediate position shown in FIG. 11 leaving a major portion of the diluted sample $(S+D_1)$ in the cylinder 27, and above all, a defined volume of first stage diluted sample in the channel 14.

Figure 11:
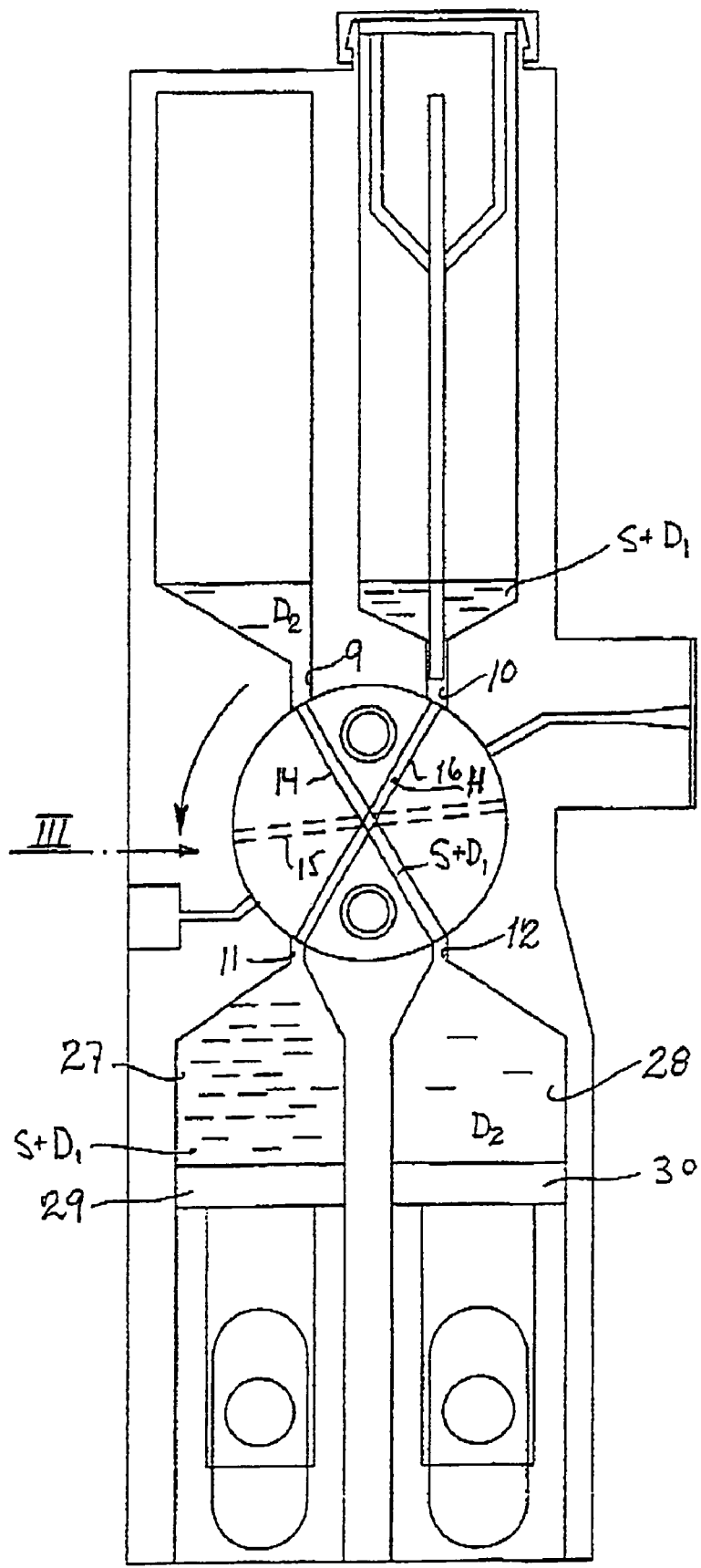
FIG. 11 is a front view of the apparatus having its plungers in an intermediate position and its valve rotated a further step to a third position.

In a following step, the turning valve is rotated counterclockwise to its third position III, where its channel 14 connects channels 9 and 12, and its channel 16 connects the channels 10 and 11 (FIG. 11). In this rotational position, channel 14 contains a defined volume of sample S and diluting agent $D_1$ $(S+D_1)$, whereas channel 16 still contains its original contents of haemolysis agent H.

Figure 12:
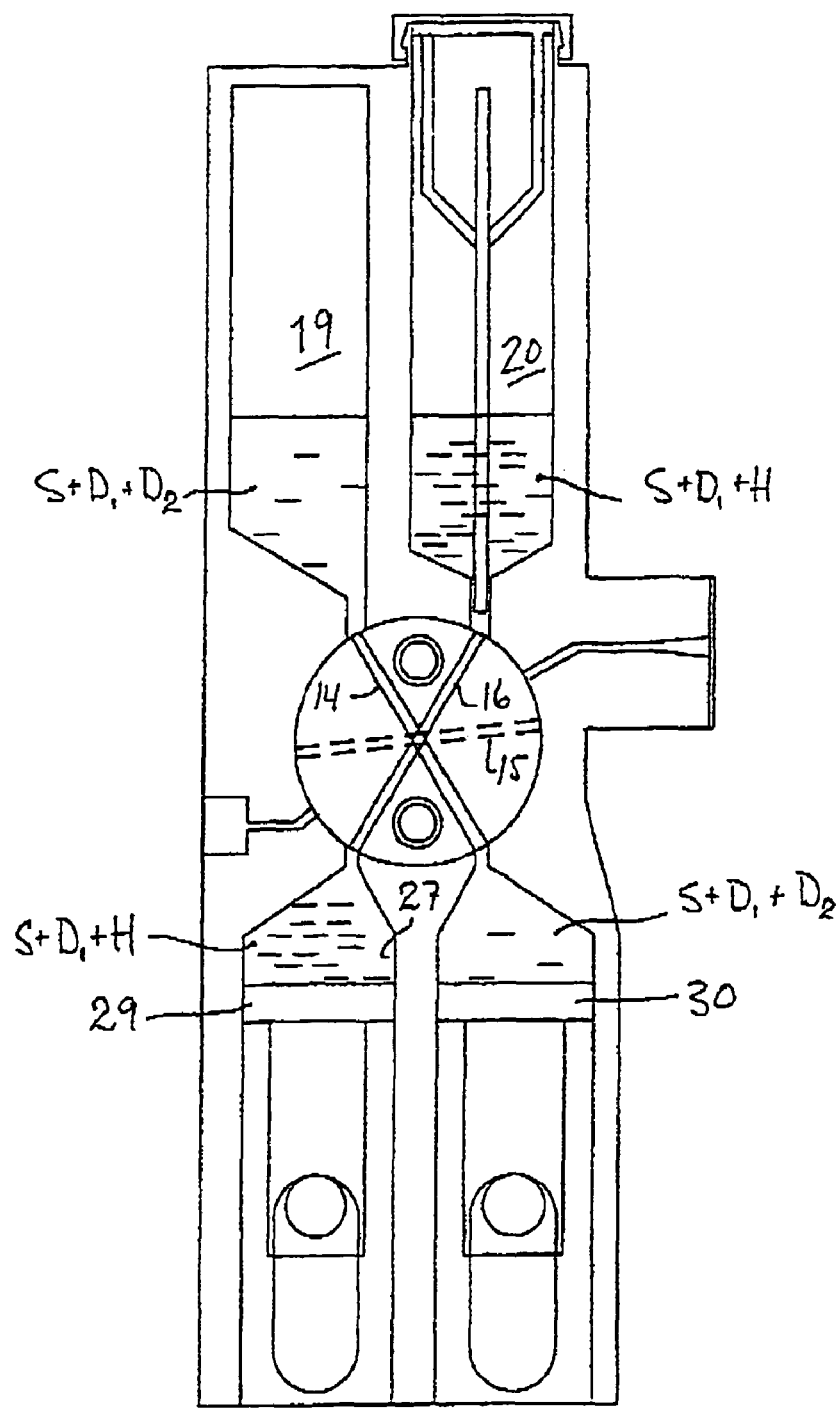
FIG. 12 is a front view of the apparatus having its valve in the third position and its plungers displaced to their extreme positive position.
Figure 12:
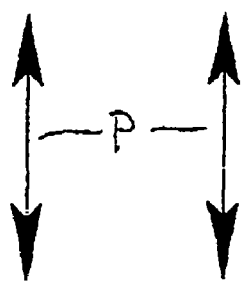

Upward movement of the piston 29 as shown in FIG. 12, displaces the diluted sample $(S+D_1)$ through the valve channel 16 to convey the haemolysis agent H therefrom into the recipient 20 to mix with the first stage mixture $(S+D_1)$ to form a mixture $(S+D_1+H)$. Simultaneous upward movement of piston 30 displaces the diluting agent $D_2$ from the cylinder 28 through the valve channel 14 containing a defined volume of first stage diluted sample $S+D_1$. This first stage sample, thus, will be mixed with the volume of diluting agent $D_2$ present in recipient 19 to provide a second stage diluted sample $(S+D_1+D_2)$. Subsequent reciprocating movement of the pistons will complete the two simultaneous mixing processes, leaving a final dilution ratio of typically 1:200 in the cylinder 27 and the receptacle 20, and a final dilution ratio of typically 1:40000 in the cylinder 28 and the receptacle 19.

After this final dilution step, the measurements on the two differently diluted samples $(S+D_1+H)$ and $(S+D_1+D_2)$ are performed with the instrument mentioned. Apart from its operating arms, the instrument includes a measuring system having means for conducting at least parts of the contents in the receptacles 19 and 20 past measurement stations, where particle counting is performed, as well as means for controlling the volumes to be measured and means for flushing the various conduits of the measuring system. Such means are shown in FIGS. 8, 9, 13 and 14.

The measuring system includes two similar conduit branches 45a, 45b, one for each of the receptacles 19, 20. Each such branch starts with a needle portion 46a, 46b directed in parallel with the arms 38-41 so as to pierce corresponding diaphragms 47a, 47b sealing apertures 48a, 48b in the rear housing wall 7 communicating with the receptacles 19, 20, respectively.

The needle portions are in fluid communication with conduits 49a, 49b. These are provided with cell counting stations 50a, 50b, each comprising a first electrode 51a, 51b, an orifice 52a, 52b and a second electrode 53a, 53b. The orifices are small apertures allowing statistically only one blood cell to pass at a time. By means of electric wires 54a, 55a and 54b, 55b, respectively, a voltage may be applied over the orifices, and any change in the resistance between the electrodes, indicating the passage of a blood cell to be counted, may be detected by suitable electronic equipment included in the instrument, and the sum of all resistance changes detected corresponds to the number of blood cells having passed through the orifice.

Each of the conduits 49a, 49b is branched into two sub-branch conduits 56a, 56b and 57a, 57b, respectively. The conduits 56a, 56b lead to a respective container 58a, 58b containing a flush liquid F. The flush liquid also fills the conduits 56a, 56b as well as the conduits 49a, 49b including the needle portions 47a, 47b. Valves 59a, 59b are mounted in the conduits 56a, 56b between the containers 58a, 58b and the sub-branch conduits 57a, 57b, respectively. Valves 60a, 60b are also mounted in the conduits 57a, 57b. The flush liquid F is filled into the conduits 56a, 56b to a level LF above the valves 60a, 60b.

Substantially vertical portions of the conduits 57a, 57b are provided with lower counting start detectors 61a, 61b and upper counting stop detectors 62a, 62b spaced defined distances.

Figure 13:
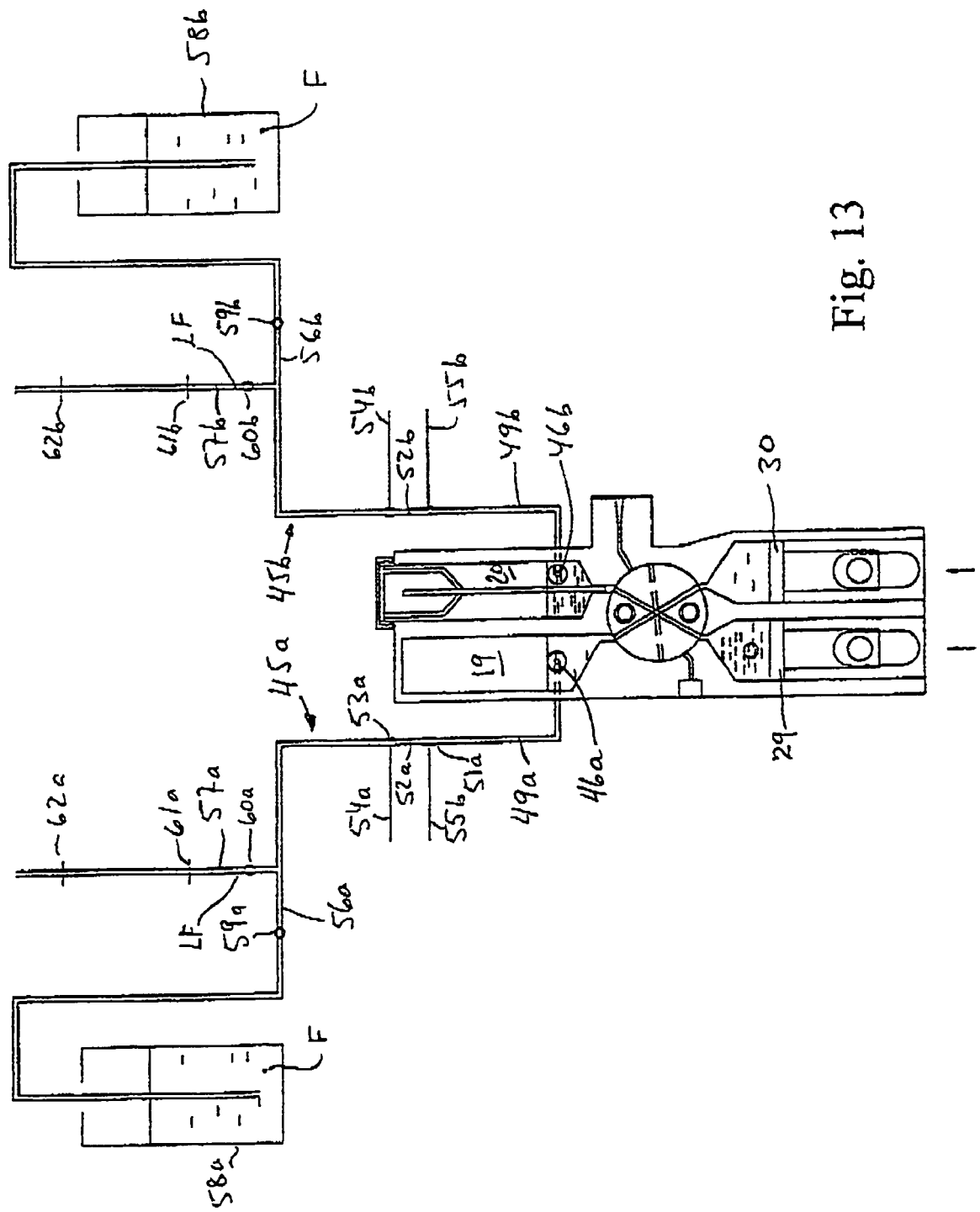
FIG. 13 is a view corresponding to that of FIG. 8, but showing the valve in its third position and its plungers moving towards their extreme positive positions.

After completing the simultaneous mixing operations described above with reference to FIG. 12, and before commencing the particle counting process, the valves 59a, 59b are closed, whereas the valves 60a, 60b are opened. Furthermore, the pistons 29, 30 must be brought to positions where the levels in the receptacles 19 and 20 are located above the needle portions 46a, 46b, as seen in FIG. 13.

From these positions, the pistons are further displaced upwards to press the respective contents of the receptacles 19, 20 through the needle portions 46a, 46b and into the conduits 49a, 49b. During this process, the flush liquid contained within the needle portions and the conduits will be displaced through the conduits 49a, 49b, including the electrodes 51a, 51b, the orifices 52a, 52b and the electrodes 53a, 53b, through the open valves 60a, 60b to raise the original level LF towards the respective lower detector 61a, 61b.

It should be emphasised at this stage of the description, that the various conduits shown in the drawings are not drawn in proper relative scales. In practice, and as will be evident for the skilled person, the volumes within the conduits 49a, 49b, including the needle portions 47a, 47b, up to the second electrodes 53a, 53b, are at least equal to the volumes within the conduits 57a, 57b between the valves 60a, 60b and the counting start detectors 61a, 61b.

In other words, the dimensioning of the conduits is such, that when the levels of the flush liquid in the vertical conduits 57a, 57b have reached the counting start detectors 61a, 61b, the respective diluted sample shall at least have reached its associated second electrode 53a, 53b, respectively.

Thus, when the level of the flush liquid has reached the respective counting start detector 61a, 61b, a signal is delivered to the instrument to start particle counting, i.e., to start recording each resistance change detected over the electrodes 51a, 53a and 51b, 53b, respectively. As soon as the levels LF in the conduits 57a, 57b have reached the respective upper detector 62a, 62b, a stop counting signal is delivered to the instrument, and the corresponding results may be stored in the instrument and/or displayed on it.

During the counting process, the diluted blood samples never reach further along the conduits than to positions well before the respective branching point 49' of the conduits 49a, 49b.

After the counting process has been completed, the pistons 29, 30 are returned to positions where the levels LF in the conduits 57a, 57b are substantially as before starting the counting.

Figure 14:
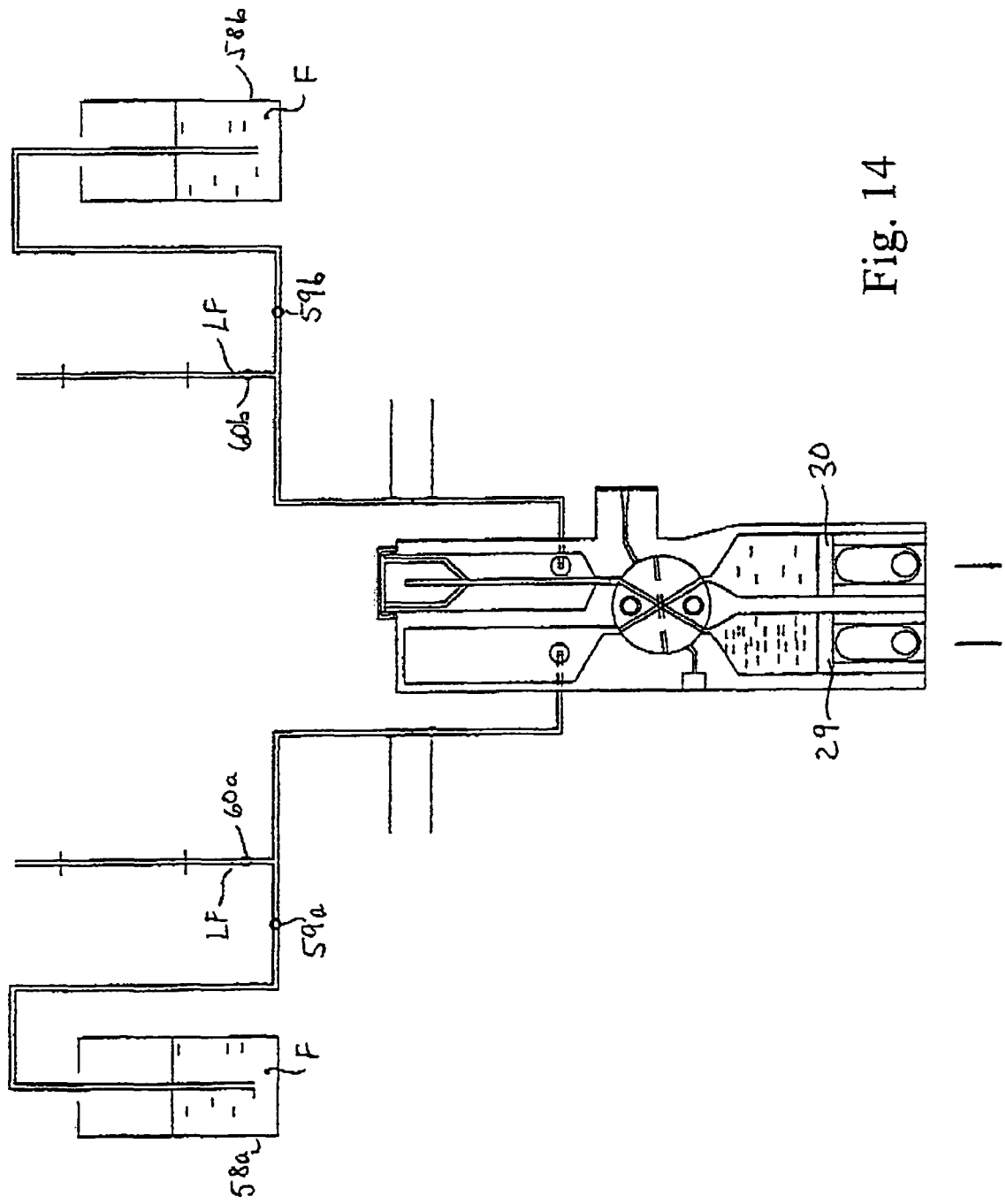
FIG. 14 is a view corresponding to that of FIG. 13, but showing the plungers in their extreme negative position after having performed a flush stroke.

At this stage, the valves 60a, 60b are closed, the valves 59a, 59b are opened, and the pistons 29, 30 are lowered to their bottom positions as shown in FIG. 14. During this process, flushing liquid F is withdrawn from the respective container 58a, 58b through the conduits 56a, 56b to completely flush through the conduits 49a, 49b, including the second electrodes 53a, 53b, the orifices 52a, 52b, the first electrodes 51a, 51b, and the needle portions 46a, 46b.

In this position, all possibly contaminated liquid is contained within the cylinders 27, 28. When finally removing the disposable apparatus housing 1 from the instrument, the elastic diaphragms 47a, 47b will effectively wipe off any diluted sample residue from the needle portions 46a, 46b.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A disposable apparatus for simultaneously preparing two diluted samples for testing on a blood testing instrument, said disposable apparatus comprising:

a housing formed therein a first closed receptacle and a first container for preparing a first diluted sample, each connected to one of a first pair of channels, said first container containing a defined volume of first liquid agent; and a second closed receptacle and a second container for preparing a second diluted sample, each connected to one of a second pair of channels, said second container containing a defined volume of a second liquid agent;

a valve disposed in said housing, positionable in distinct positions, at one position said valve connecting said first receptacle and said first container through said first pair of channels, and connecting said second receptacle and said second container through second pair of channels, simultaneously through said valve; and an opening on said housing connected to said valve through a channel, for introducing a blood sample into said valve;

wherein at said one position of said valve, a mixture of said first liquid agent and a first part of said blood sample introduced by said valve is caused to move back and forth between said first receptacle and said first container through said valve, thereby forming said first diluted sample, and a mixture of said second liquid agent and a second part of said blood sample introduced by said valve is caused to move back and forth between said second receptacle and said second container through said valve, thereby forming said second diluted sample.

2. The disposable apparatus of claim 1 further comprising sealed apertures on a wall of said housing communicating with said receptacles, adapted to be pierced for delivery of said diluted samples.

3. The disposable apparatus of claim 1, wherein said valve is a turning valve or a sliding valve.

4. The disposable apparatus of claim 1, wherein said valve comprises multiple valve channels.

5. The disposable apparatus of claim 4, wherein at said one position said mixtures pass through at least two of said valve channels, respectively.

6. The disposable apparatus of claim 1 further comprises two pistons, each disposed within one of said containers.

7. The disposable apparatus of claim 6, wherein said mixtures are caused to move back and forth between respective receptacles and containers by reciprocating movement of respective pistons.

8. The disposable apparatus of claim 1, wherein said mixtures are caused to move back and forth between respective receptacles and containers by an external source of pressure.

9. The disposable apparatus of claim 1, wherein moving said first liquid agent from said first container into said first receptacle brings along said first part of said blood sample introduced in said valve, and moving said second liquid agent from said second container into said second receptacle brings along said second part of said blood sample introduced in said valve.

10. The disposable apparatus of claim 1, wherein said first diluted sample and said second diluted sample have different dilution ratios.

11. The disposable apparatus of claim 1 further comprising a hemolysis agent.

12. A system for testing a blood sample comprising:
(a) a disposable apparatus comprising:
a housing formed therein a first closed receptacle and a first container for preparing a first diluted sample, each connected to one of a first pair of channels, said first container containing a defined volume of first liquid agent; and a second closed receptacle and a second container for preparing a second diluted sample, each connected to one of a second pair of channels, said second container containing a defined volume of a second liquid agent;
a valve disposed in said housing, positionable in distinct positions, at one position said valve connecting said first receptacle and said first container through said first pair of channels, and connecting said second receptacle and said second container through second pair of channels, simultaneously through said valve; and
an opening on said housing connected to said valve through a channel, for introducing a blood sample into said valve;
wherein at said one position of said valve, a mixture of said first liquid agent and a first part of said blood sample introduced by said valve is caused to move back and forth between said first receptacle and said first container through said valve, thereby forming said first diluted sample, and a mixture of said second liquid agent and a second part of said blood sample introduced by said valve is caused to move back and forth between said second receptacle and said second container through said valve, thereby forming said second diluted sample; and
(b) an instrument comprising:
operating arms adapted to position said valve of said disposable apparatus at one of said distinct positions for receiving a blood sample and at another of said positions for diluting said blood sample;
measurement stations for particle counting; and
conduits adapted to fluidly connect said first and second receptacles of said disposable apparatus, respectively, to said measurement stations.

13. The system of claim 12, wherein said instrument further comprises actuating means adapted to move pistons disposed in said first and second containers.

14. A method of simultaneously preparing two diluted samples for testing on a blood testing instrument, comprising:
(a) receiving a blood sample through an opening into a valve of a disposable apparatus, said disposable apparatus comprising:
a housing including a first closed receptacle and a first closed container for preparing a first diluted sample, each connected to one of a first pair of channels, said first container containing a defined volume of first liquid agent; and a second closed receptacle and a second closed container for preparing a second diluted sample, each connected to one of a second pair of channels, said second container containing a defined volume of second liquid agent; said opening on said housing connected to said valve through a channel; and said valve disposed in said housing, positionable in distinct positions;
(b) positioning said valve to one position to connect said first receptacle and said first container through said first pair of channels, and to connect said second receptacle and said second container through second pair of channels, simultaneously through said valve;
(c) causing a mixture of said first liquid agent and a first part of a blood sample in said valve to move back and forth between said first receptacle and said first container through said valve, thereby forming said first diluted sample; and causing a mixture of said second liquid agent and a second part of said blood sample in said valve to move back and forth between said second receptacle and said second container through said valve, thereby forming said second diluted sample.

15. The method of claim 14, wherein said first diluted sample and said second diluted sample have different dilution ratios.

16. The method of claim 14, wherein said valve is a turning valve or a sliding valve.

17. The method of claim 14, wherein moving said first liquid agent from said first container into said first receptacle brings along said first part of said blood sample in said valve, and moving said second liquid agent from said second container into said second receptacle brings along said second part of said blood sample in said valve.

18. The method of claim 14, wherein said valve comprises multiple valve channels.

19. The method of claim 18, wherein at said one position said mixtures pass through at least two of said valve channels, respectively.

20. The method of claim 14, wherein said mixtures are caused to move back and forth between respective receptacles and containers by displacers.

21. The method of claim 20, wherein said displacers are two pistons, each disposed within one of said containers, and said mixtures are caused to move back and forth between respective receptacles and containers by reciprocating movements of said pistons.

22. The method of claim 21, wherein said displacers are an external source of pressure.

23. The method of claim 14 further comprising mixing one of said mixtures with a hemolysis agent contained in said disposable apparatus.

24. The method of claim 19 further comprising delivering said first and second diluted samples from said first and second receptacles, respectively, to said blood testing instrument for measurements.

25. The method of claim 24, wherein said delivering is effected by piercing sealed apertures on said housing, each communicating with one of said receptacles, and transferring said first and second diluted samples, respectively, through conduits of said blood testing instrument.

26. The method of claim 25 further comprising measuring said first and second diluted samples on said blood testing instrument to measure white blood cells and red blood cells.

* * * * *

UNITED STATES PATENT AND TRADEMARK OFFICE
CERTIFICATE OF CORRECTION

PATENT NO. : 8,012,432 B2  Page 1 of 1
APPLICATION NO. : 11/493697
DATED : September 6, 2011
INVENTOR(S) : Berndtsson It is certified that error appears in the above-identified patent and that said Letters Patent is hereby corrected as shown below:

ON THE TITLE PAGE:
At Item (63), correct the Related U.S. Application Data to read as follows:

--(63)   Related U.S. Application Data

Continuation of application No. 10/849,239, which is a continuation of application No. PCT/SE02/02093, filed on Nov. 18, 2002, now U.S. Patent 7,335,339.--.

Insert the following Foreign Application Priority Data:

--(30)   Foreign Application Priority Data

Nov. 21, 2011 (SE) ................ 0103877-7--.

Signed and Sealed this
Twenty-ninth Day of November, 2011

David J. Kappos
*Director of the United States Patent and Trademark Office*